(12) United States Patent
Hu et al.

(10) Patent No.: US 8,426,407 B2
(45) Date of Patent: Apr. 23, 2013

(54) PREPARATION OF 1-(SUBSTITUTED ARYL)-5-TRIFLUOROMETHYL-2-(1H)PYRIDONE COMPOUNDS AND SALTS THEREOF AND THEIR APPLICATIONS

(75) Inventors: Gaoyun Hu, Changsha (CN); Lijian Tao, Changsha (CN); Jun Chen, Changsha (CN)

(73) Assignee: Central South University, Changsha (CN)

( * ) Notice: Subject to any disclaimer, the term of this patent is extended or adjusted under 35 U.S.C. 154(b) by 0 days.

(21) Appl. No.: 13/322,152

(22) PCT Filed: May 24, 2010

(86) PCT No.: PCT/CN2010/073105
§ 371 (c)(1),
(2), (4) Date: Feb. 8, 2012

(87) PCT Pub. No.: WO2010/135972
PCT Pub. Date: Dec. 2, 2010

(65) Prior Publication Data
US 2012/0142688 A1    Jun. 7, 2012

(30) Foreign Application Priority Data

May 25, 2009   (CN) .......................... 2009 1 0043501

(51) Int. Cl.
*A61K 31/5377* (2006.01)
*A61K 31/497* (2006.01)
*A61K 31/4427* (2006.01)
*A61K 31/44* (2006.01)
*C07D 413/02* (2006.01)
*C07D 401/02* (2006.01)
*C07D 211/06* (2006.01)
*C07D 211/80* (2006.01)

(52) U.S. Cl.
USPC ................... 514/235.5; 514/253.12; 514/318; 514/345; 544/131; 544/360; 546/255; 546/290

(58) Field of Classification Search ............... 514/235.5, 514/253.12, 318, 345; 544/131, 360; 546/255, 546/290
See application file for complete search history.

(56) References Cited

FOREIGN PATENT DOCUMENTS

| | | |
|---|---|---|
| CN | 1646125 A | 7/2005 |
| CN | 1878757 A | 12/2006 |
| CN | 101235030 A | 8/2008 |
| CN | 101237869 A | 8/2008 |
| CN | 101371833 A | 2/2009 |
| WO | WO-2005009392 A2 | 2/2005 |
| WO | WO-2006122154 A2 | 11/2006 |
| WO | WO-2007/053685 A2 | 5/2007 |
| WO | WO-2007/062167 A2 | 5/2007 |
| WO | WO-2008154207 A1 | 12/2008 |
| WO | WO-2009149188 A1 | 12/2009 |
| WO | WO-2010/085805 A1 | 7/2010 |
| WO | WO-2010/135470 A1 | 11/2010 |

OTHER PUBLICATIONS

Database Accession No. 339024-94-1, Chemical Abstracts Service, Columbus, Ohio, XP-002684268, May 30, 2001.
Database Accession No. 764691-46-5, Chemical Abstracts Service, Columbus, Ohio, XP-002684269, Oct. 18, 2004.
Database Accession No. 768724-02-5, Chemical Abstracts Service, Columbus, Ohio, XP-002684270, Nov. 23, 2004.
Database Accession No. 685542-68-1, Chemical Abstracts Service, Columbus, Ohio, XP-002684271, May 25, 2004.
Extended European Search Report dated Oct. 12, 2012, issued in corresponding European Application No. 10780057.5 to copending U.S. Appl. No. 13/322,153.

*Primary Examiner* — Rebecca Anderson
(74) *Attorney, Agent, or Firm* — Birch, Stewart, Kolasch & Birch, LLP

(57) ABSTRACT

A 1-(substituted aryl)-5-trifluoromethyl-2-(1H)pyridone compounds and pharmaceutical acceptable salts, preparation methods and uses for preparing the drugs for treating fibrosis thereof.

5 Claims, 1 Drawing Sheet

PREPARATION OF 1-(SUBSTITUTED ARYL)-5-TRIFLUOROMETHYL-2-(1H)PYRIDONE COMPOUNDS AND SALTS THEREOF AND THEIR APPLICATIONS

This application is a U.S. National Phase of the International Application No. PCT/CN2010/073105 filed on 24 May 2010 designating the U.S. and published on 2 Dec. 2010 as WO 2010/135972.

TECHNICAL FIELD

The invention relates to 1-(substituted aryl)-5-trifluoromethyl-2-(1H)pyridone compounds, preparation methods and medical applications for the same.

BACKGROUND OF THE INVENTION

In a variety of organs or tissues, fibrosis causes reduction of parenchyma cells therein and an increase of fibrous connective tissues, eventually damaging tissue structures, causing tissue dysfunction or even organ failure. The mechanism of fibrosis, and diagnostic methods and prevention measures for fibrosis of organs or tissues have been widely studied. In prior art, considerable progress has been made in some aspects, but some key unresolved issues still exist.

U.S. Pat. Nos. 3,839,346A, 4,052,509A, 4,042,699 disclose 29 pyridone compounds having formula I as follows,

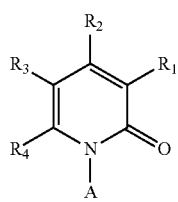

Formula I and disclose functions of the pyridone compounds of resisting inflammation, allaying fever, reducing the level of serum uric acid, relieving pain or the like, wherein 5-methyl-1-phenyl-2(1H)-pyridone (Pirfenidone) has the best activity and lower toxicity.

U.S. Pat. No. 5,310,562 discloses 5-methyl-1-phenyl-2(1H)-pyridone for the first time in 1994, that is Pirfenidone (PFD), having an anti-fibrosis biological activity; subsequently U.S. Pat. Nos. 5,518,729 and 5,716,632 disclose N-substituted-2-(1H)pyridone described as the structural formula I and N-substituted-3-(1H)pyridone having the same anti-fibrosis function. Forty-four compounds are specified, most of which are known compounds derived from U.S. Pat. No. 4,052,509; and in the compounds, R1, R2, R3, and R4 are defined as methyl groups or ethyl groups.

Pirfenidone (PFD) is proven to have effectiveness in fibrosis prevention through in vitro and animal experiments. Pirfenidone has functions of stopping or even converting ECM accumulation and preventing or reversing fibrosis and scar formation in experiments using animals with renal fibrosis and pulmonary fibrosis and in the clinical treatment of patients with idiopathic pulmonary fibrosis. (Shimizu T, Fukagawa M, Kuroda T, et al. Pirfenidone prevents collagen accumulation in the remnant kidney in rats with partial nephrectomy. Kidney Int, 1997,52 (Suppl 63): S239-243; Raghu G, Johnson W C, Lockhart D, et al. Treatment of idiopathic pulmonary fibrosis with a new antifibrotic agent, pirfenidone. Am J Respir Crit Care Med, 1999,159: 1061-1069). The applicant proposes a CN patent ZL02114190.8 and provides a class of pyridone compounds of the formula II.

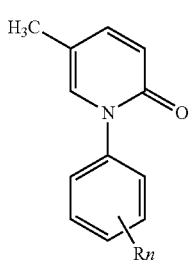

Formula II

In the structural formula II, if n=1, the substituent R is F, Br, or I; if n=2, the substituents R are F, Cl, Br, I, a saturated linear alkyl group, an oxo-saturated linear alkyl group, or a halo-saturated linear alkyl group. The substituent R is at any of the ortho-position, meta-position, and para-position on a benzene ring.

Pirfenidone came into the market in Japan in 2008 for treating indications for pulmonary fibrosis. However, Pirfenidone and its derivatives do not have high enough strength. The clinical dose of Pirfenidone achieves 2400 mg/day.

Patent publications WO 2007053685 and WO 2006122154 disclose compounds having functions of inhibiting p38 kinase, applied to treatment of fibrosis diseases and disclose the formula III;

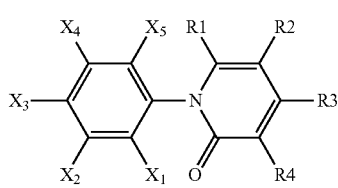

Formula III wherein, R1-R4 each are H, an alkyl group, a substituted alkyl group, an alkenyl group, a haloalkyl group, a nitro alkyl group, a hydroxyalkyl group, an alkoxyl group, a phenyl group, a substituted phenyl group, halogen, a hydroxyl group, an alkoxyalkyl group, a carboxyl group, an alkoxycarbonyl group, etc.; X1-X5 each are H, halogen, an alkoxyl group, or a hydroxyl group.

WO 2007062167 also discloses compounds having functions of inhibiting p38 kinase and applied to treatment of various fibrosis diseases, wherein some structures are shown as follows:

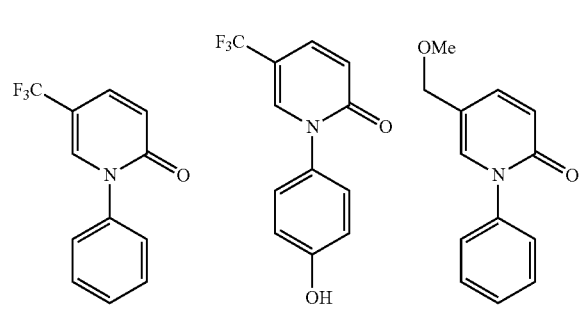

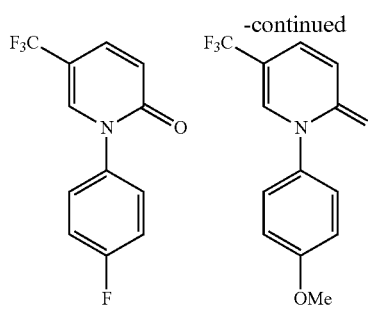

Some simple substituents are provided on the benzene rings of the compounds.

CN patent 200710034357 discloses some similar compounds having the above structures with anti-fibrosis activity and a compound with the anti-fibrosis activity shown in the formula IV.

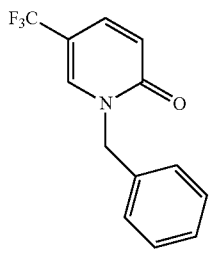

Formula IV

Those compounds are provided with TFM at the 5-position of the pyridone ring, thereby overcoming the disadvantages of inferior action of Pirfenidone, but the strength of those compounds is still not powerful enough.

DE patent DE4343528 reports a class of compounds having insecticidal actions for agricultural use, with the formula V as follows.

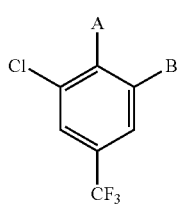

Formula V

In structural formula V, A and B are substituted by various heterocyclic rings, such as furan, imidazole, pyridine and pyridone; wherein a class of compounds with the formula VI is included.

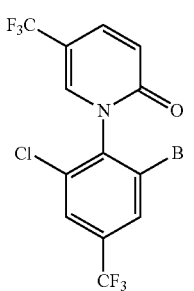

Formula VI

EP patents EP259048, EP367410 and EP398499 report a class of compounds having insecticidal actions for use in agriculture, with the formula VII as follows:

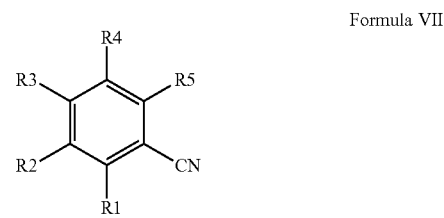

Formula VII wherein a class of compounds having the formula VIII, in which R1 is pyridone and R10 is O or S, is included.

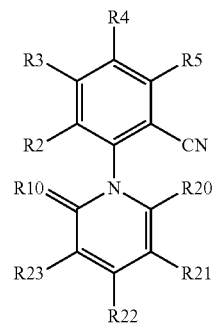

Formula VIII

EP patent EP216541 reports a class of compounds having insecticidal actions for use in agriculture, with the formula IX as follows:

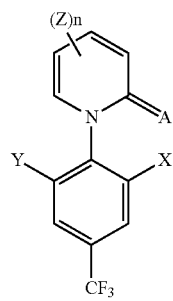

Formula IX wherein a class of compounds with the formula X is included.

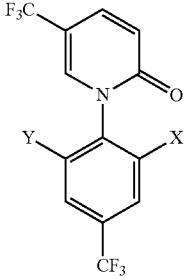

Formula X

EP patent EP488220 reports a class of compounds having insecticidal actions, with the formula XI as follows:

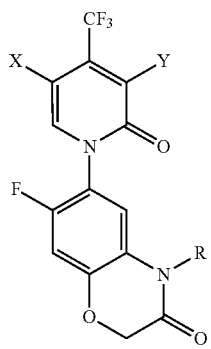

Formula XI

In structures of the above-mentioned compounds, the pyridine ring and the benzene ring at the 1-position of the pyridine ring have a plurality of substituents; the compounds with complicated structures have not been reported to have the anti-fibrosis function.

DE102004027359 discloses a class of compounds capable of modulating dopamine-3 receptor and applied to treatment of Parkinson's disease and schizophrenosis;

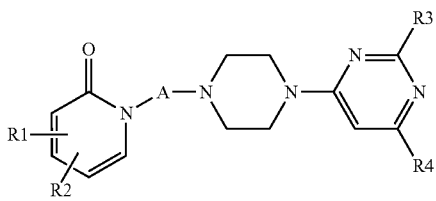

Formula XII wherein, A is a hydrocarbon chain with 4-6 atoms, having 1-2 substituted methyl groups thereon; or 1-2 carbon atoms in the carbon chain are substituted by O, C=O, S and other atoms; R1 and R2 are H, CN, $NO_2$, halogen atom, $OR^5$, $NR^6R^7$, $C(O)NR^6R^7$, $O—C(O)NR^6R^7$; a $C_1$-$C_6$ alkyl group, a $C_1$-$C_6$ haloalkyl group, etc.

Accordingly, compounds in the prior art have low anti-fibrosis activities and strong liposolubility as a plurality of fluorine atoms are introduced onto molecules. As a result, the compounds cannot be made into solutions because there is no highly water-soluble group in the molecule.

SUMMARY OF THE INVENTION

The invention provides 1-(substituted phenyl)-5-trifluoromethyl-2-(1H)pyridine compounds shown in formula XIII,

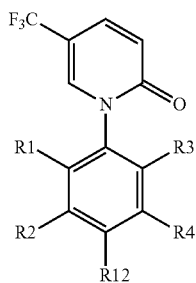

Formula XIII wherein R1-R4, R12 are selected from H, CN, $NO_2$, a hydroxyl group, an amino group, a halogen atom, a $C_1$-$C_6$ alkoxyl group, $NR^{10}R^{11}$, $OR^{13}$, $C(O)R^{14}$, $O$–$C(O)R^{14}R^{15}$, a $C_1$-$C_6$ alkyl group, a $C_1$-$C_6$ haloalkyl group, a $C_2$-$C_6$ alkenyl group, a carboxyl group and carboxylic ether; wherein $R^{14}$ and $R^{15}$ are a $C_1$-$C_6$ alkyl group, $R^{10}$ and $R^{11}$ are selected from H, a $C_1$-$C_6$ hydroxyalkyl group, an esterified $C_1$-$C_6$ hydroxyalkyl group, a $C_1$-$C_6$ alkoxyalkyl group, or formula XIV; and at least one of R1-R4 and R12 is $NR^{10}R^{11}$ or $OR^{13}$; in $OR^{13}$, $R^{13}$ is a $C_1$-$C_6$ hydroxyalkyl group or a $C_1$-$C_6$ alkoxyalkyl group; and $R^{10}$ and $R^{11}$ are not simultaneously H;

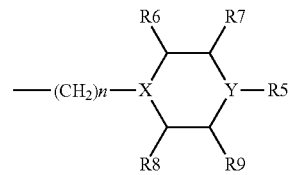

Formula XIV in formula XIV, R5 is selected from H, a $C_1$-$C_6$ alkyl group, a $C_1$-$C_6$ haloalkyl group, a $C_1$-$C_6$ hydroxyalkyl group, an esterified $C_1$-$C_6$ hydroxyalkyl group, and a $C_2$-$C_6$ alkenyl group; R6-R9 are selected from H, a $C_1$-$C_6$ alkoxyl group, =O, a $C_1$-$C_4$ alkyl group, a $C_1$-$C_4$ haloalkyl group, a $C_1$-$C_4$ hydroxyalkyl group, and a $C_2$-$C_4$ alkenyl group; X is selected from N and CH; Y is selected from N, O, and C (with the proviso that, when Y is O, R5 is absent; and n is 1-6; and pharmaceutically available salts thereof.

More preferably, R12 is $NR^{10}R^{11}$ or $OR^{13}$.

According to embodiments of the invention, more preferably, one of R1-R4 is a halogen atom and others are H if R12 is $NR^{10}R^{11}$ or $OR^{13}$.

According to embodiments of the invention, the following compounds are preferred:

1-(2-chloro-4-((3-(4-methylpiperazin-1-yl)propyl)amino) phenyl)-5-(trifluoromethyl)pyridin-2(1H)-one (compound 1);

1-(2-chloro-4-((3-morpholinylpropyl)amino)phenyl)-5-(trifluoromethyl)pyridin-2(1H)-one (compound 2);

1-(2-chloro-4-((3-piperidin-1-yl)propylamino)phenyl)-5-(trifluoromethyl)pyridin-2(1H)-one (compound 3);

1-(4-((3-butoxypropyl)amino)-2-chlorophenyl)-5-(trifluoromethyl) pyridin-2(1H)-one (compound 4);

1-(2-chloro-4-((2-hydroxyethyl)amino)phenyl)-5-(trifluoromethyl)pyridin-2(1H)-one (compound 5);

1-(4-(N,N-(2-hydroxyethyl)amino)-2-chlorophenyl)-5-(trifluoromethyl)pyridin-2(1H)-one (compound 6);

1-(2-chloro-4-(((3-piperidin-1-yl)propyl)amino)phenyl)-5-(trifluoromethyl)pyridin-2(1H)-one hydrochloride (compound 7);

1-(2-chloro-4-((2-(2-hydroxyethoxy)ethyl)amino)phenyl)-5-(trifluoromethyl)pyridin-2(1H)-one (compound 8);

1-((4-((piperazin-1-yl)ethyl)amino)-2-chlorophenyl)-5-(trifluoromethyl)pyridin-2(1H)-one (compound 9);

1-(2-chloro-4-((2-(piperidyl-1-yl)ethyl)amino)phenyl)-5-(trifluoromethyl)pyridin-2(1H)-one (compound 10);

1-(2-chloro-4-((2-morpholinylethyl)amino)-phenyl)-5-(trifluoromethyl)pyridin-2(1H)-one (compound 11);
1-(2-chloro-4-((2-(4-methylpiperazin-1-yl)ethyl)amino)phenyl)-5-(trifluoromethyl)pyridin-2(1H)-one (compound 12);
1-(2-chloro-4-((2-(4-(2-hydroxyethyl)piperazin-1-yl)ethyl)amino)-phenyl)-5-(trifluoromethyl)pyridin-2(1H)-one (compound 13),
and pharmaceutically acceptable salts, including hydrochlorate, sulfate, phosphate, perchlorate, methanesulfonate, trifluoromethanesulfonate, formate, acetate, propionate, butyrate, maleate, succinate, trifluoroacetate, succinate, salicylate, DL-aspartate, D-aspartate, L-aspartate, DL-glutamate, D-glutamate, L-glutamate, glycerate, succinate, stearate, DL-tartrate, D-tartrate, L-tartrate, (+/−)-mandelate, (R)-(−)-mandelate, (S)-(+)-mandelate, citrate, mucate, maleate, malonate, benzoate, DL-malate, D-malate, L-malate, hemimalate, 1-adamantane acetate, 1-adamantane carboxylate, flavianate, sulfoacetate, (+/−)-lactate, L-(+)-lactate, D-(−)-lactate, pamoate, D-α-galacturonic acid salt, glycerate, DL-cystine salt, D-cystine salt, L-cystine salt, DL-homocystine salt, D-homocystine salt, L-homocystine salt, DL-cysteine salt, D-cysteine salt, L-cysteine salt, (4S)-hydroxy-L-proline, cyclopropane-1,1-dicarboxylate, 2,2-methyl malonate, tyrosine salt, proline salt, fumarate, 1-hydroxy-2-naphthoate, phosphonoacetate, carbonate, bicarbonate, 3-phosphonopropionate, DL-pyroglutamate, D-pyroglutamate, L-pyroglutamate, toluenesulfonate, benzenesulfonate, esilate, (+/−)-camsilate, naphthalenesulfenesulfonate, 1R-(−)-camsilate, 1S-(+)-camsilate, 1,5-napadisilate, 1,2-ethanedisulphonate, 1,3-propanedisulphonate, 3-(N-morpholino) propane sulphonate, biphenyl sulphonate, isethionate, 1-hydroxy-2-naphthalenesulfenesulfonate, dihydric phosphate, potassium hydrogen phosphate, dipotassium phosphate, potassium phosphate, sodium hydrogen phosphate, disodium phosphate, sodium phosphate, sodium dihydrogen phosphate, calcium phosphate, tertiary calcium phosphate, hexafluoro phosphate, ethenyl phosphate, 2-carboxylethyl phosphate and phenyl phosphate.

The invention also provides a synthetic method for a compound of formula XIII, including: reacting 5-trifluoromethyl-2(1H)pyridone with nitro-substituted fluorobenzene, with DMSO as solvent, potassium carbonate as an acid-binding agent and sodium iodide as a catalyst so as to form a nitro substituent; reducing the nitro substituent by iron powder in the presence of hydrochloric acid to prepare a simple amino-substituted compound; and preparing target products according to different compounds, shown in reaction formula I.

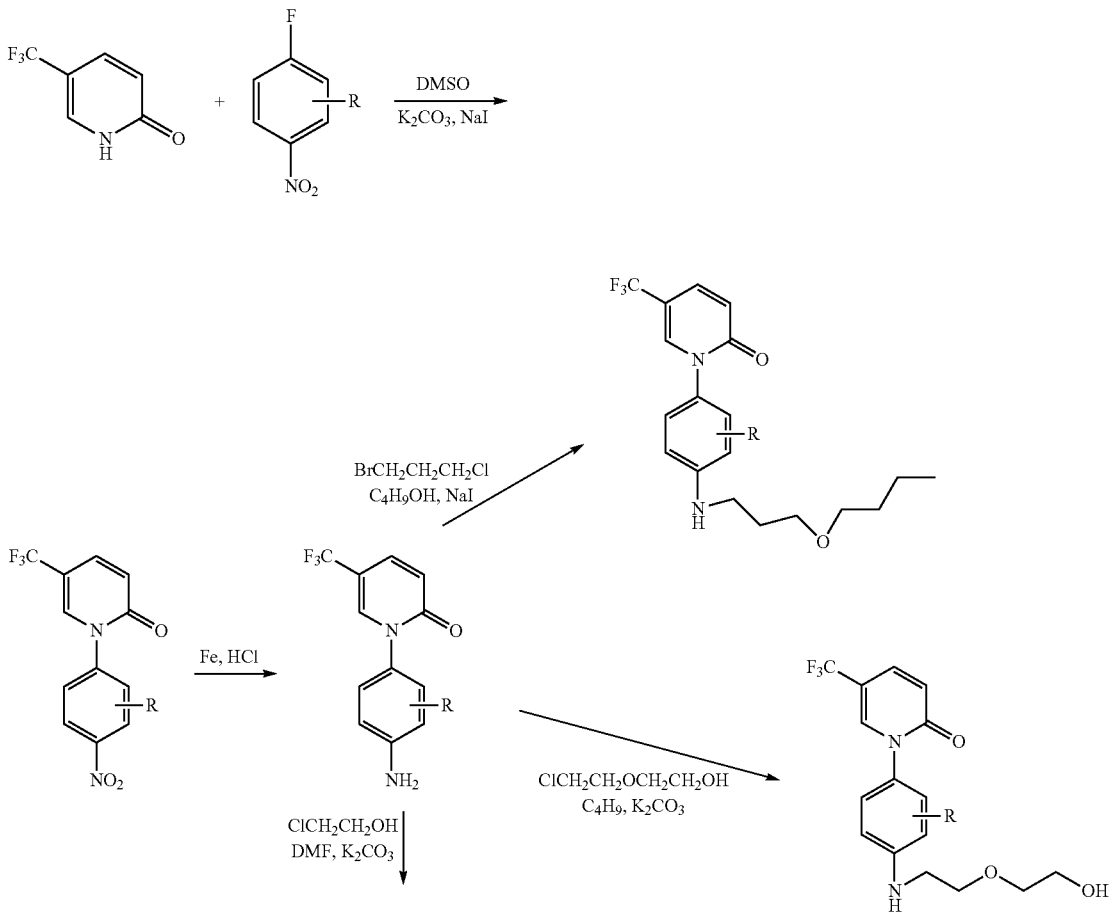

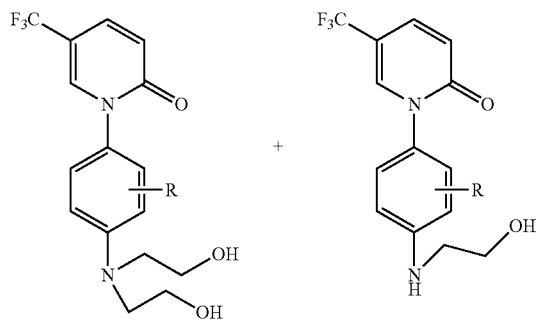

A compound, in which an amino group is bonded to a heterocyclic ring through an aliphatic side chain, is prepared by first reacting bromochloropropane with a heterocyclic compound to produce the chloroalkyl heterocyclic compound; and then reacting with the amino substituted compound prepared according to reaction formula I to obtain the target product, catalyzed by microwave irradiation, with normal butanol as solvent and sodium iodide as a catalyst, shown in the reaction formula II.

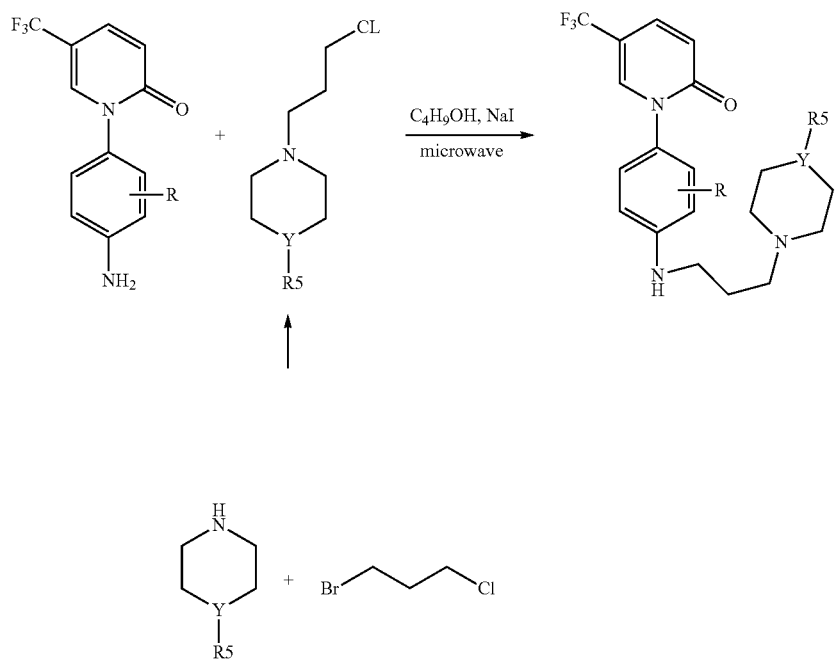

or, the target product is prepared by reacting a hydroxyethyl amino substituted compound prepared according to reaction formula I with thionyl chloride to produce the chloroethyl amino substituted compound; and then reacting with the heterocyclic compound, shown in reaction formula III.

Reaction formula III

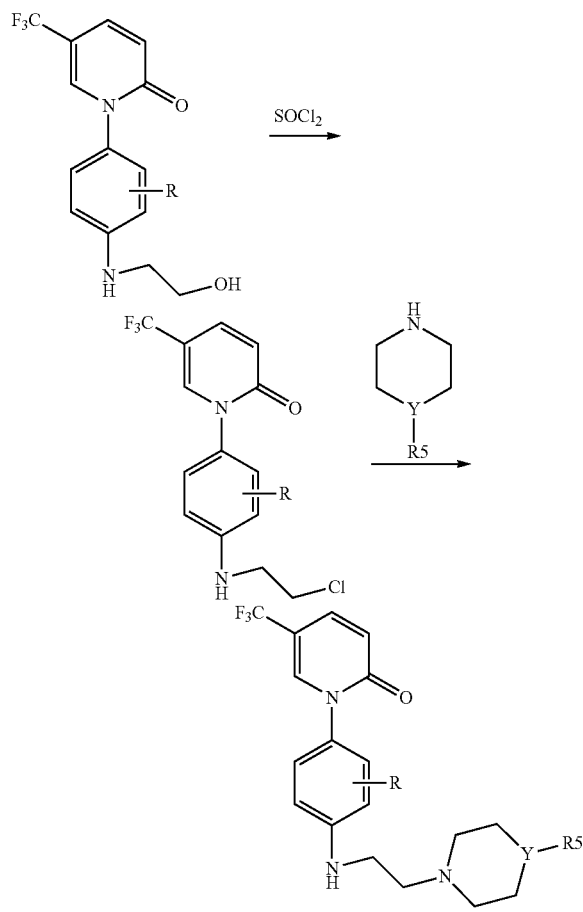

The synthetic starting product trifluoromethyl pyridone is a commercial material.

The above-mentioned compound is used for preparing a broad-spectrum medicament for fibrosis.

In the invention, based on the prior art, a substituted amino group is introduced onto the benzene ring at the 1-position of pyridone; a hydrophilic group such as a hydroxyl group and heterocyclic ring are introduced onto the amino group through an alkyl chain, thus obtaining a class of new pyridone compounds and salts thereof. The activity of the compounds is greatly enhanced.

The applicant finds that the produced compounds have relatively higher effects than the conventional pyridone compound by modifying the phenyl group by the substituted amino group on the basis of 1-phenyl-5-trifluoromethyl-pyridone; simultaneously the compounds including heterocyclic rings could be produced into various salts which are beneficial for being prepared into various liquid formulations.

The applicant learns through experiment that the compounds provided by the invention have the anti-fibrosis pharmacological action as good as the pyridone compound in the prior art, but have significantly stronger effect, over 60-fold, than the pirfenidone in the prior art. Therefore, the invention also provides applications of compounds represented by formula XIII in preparation of an anti-fibrosis medicament.

DETAILED DESCRIPTION OF PREFERRED EMBODIMENTS

Example 1

Figure 1:
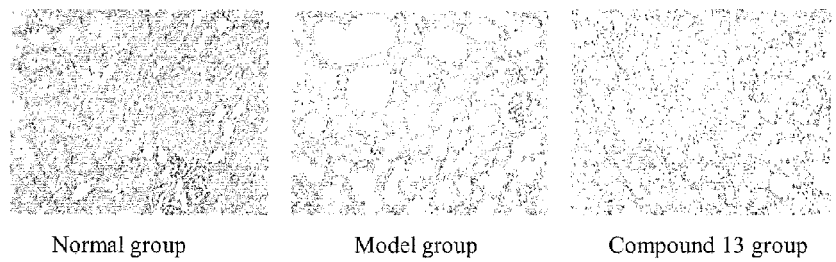
FIG. 1 HE staining for renal pathology in embodiment 15 (×200)
Figure 2:
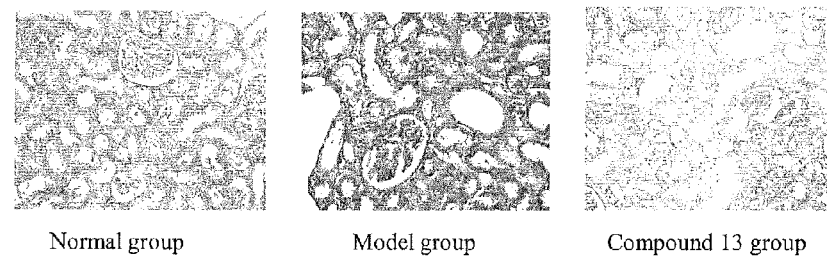
FIG. 2 Masson staining for renal pathology in embodiment 15 (×200)

Preparation of 1-(2-Chloro-4-((3-(4-Methylpiperazin-1-yl) Propyl)Amino)Phenyl)-5-(Trifluoromethyl)Pyridin-2(1H)-One (Compound 1)

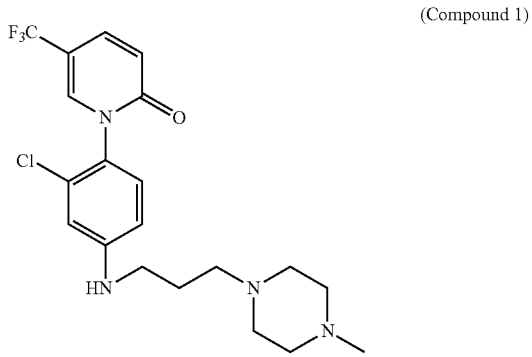 [SMILES: CN1CCN(CCCNc2ccc(-n3cc(C(F)(F)F)ccc3=O)c(Cl)c2)CC1]

A. Preparation of 1-(2-Chloro-4-Nitrophenyl)-5-(Trifluoromethyl)Pyridin-2(1H)-One The preparation of 1-(2-chloro-4-nitrophenyl)-5-(trifluoromethyl)pyridin-2(1H)-one includes steps of: adding 8.2 g (0.050 mol) of 5-(trifluoromethyl)pyridin-2(1H)-one in 100 ml of DMSO for dissolving; adding 13.1 g (0.075 mol) of 3-chloro-4-fluoronitrobenzene, 11.0 g (0.080 mol) of potassium carbonate and 1.4 g of sodium iodide and allowing the resulting system to react at 130° C. for 4 hours under stirring; after reaction, cooling to 40° C.; adding 100 ml of 12% ammonia solution; separating out a great amount of precipitate; filtering; dissolving the filter residue with ethyl acetate; decolorizing by active carbon; filtering; drying the filtrate by anhydrous sodium sulfate; filtering out sodium sulfate; reclaiming solvent; filtering to obtain the product of 1-(2-chloro-4-nitrophenyl)-5-(trifluoromethyl)pyridin-2(1H)-one. The product is 12.0 g of brown solid; m.p.: 217.7-218.3° C. MS(m/z): 318(M$^+$). $^1$H-NMR(CDCl$_3$,300 MHz) δ ppm: 6.769~6.800(d,1H,Ar-H, J=3.3 Hz), 7.579~7.570(t,3H,Ar-H), 8.296~8.333(dd,1H,J=3.3 Hz,8.7 Hz, Ar-H), 8.492(s,1H, Ar-H).

B. Preparation of 1-(4-Amino-2-Chlorophenyl)-5-(Trifluoromethyl)Pyridin-2(1H)-One The preparation of 1-(4-amino-2-chlorophenyl)-5-(trifluoromethyl)pyridin-2(1H)-one includes steps of: heating 12.0 g (0.035 mol) of 1-(2-chloro-4-nitrophenyl)-5-(trifluoromethyl)pyridin-2(1H)-one, 200 mL of 50% ethanol and 5.8 g (0.105 mol) of reductive iron powder to reflux; slowly adding 0.42 mL (0.004 mol) of concentrated HCl dropwise (dropping after dilution by 5 mL of 50% ethanol); refluxing for 5 hours under stirring; after reaction, regulating pH value to 10 by 15% KOH ethanol solution; filtering; washing the filter residues by 95% ethanol (2×10 mL); extracting by ethyl acetate (50 mL×3) after evaporating ethanol from the filtrate; drying the organic phase by anhydrous sodium sulfate overnight; filtering; and evaporating filtrate to obtain the product of 1-(4-amino-2-chlorophenyl)-5-(trifluoromethyl)pyridin-2(1H)-one. The product is 10.2 g of khaki solid powder. m.p.: 136-138° C. EI-MS(m/z): 288[M]$^+$. NMR(CDCl$_3$,300 MHz)

δ ppm: 3.559(br,2H,—NH$_2$),6.633~6.670(dd,1H,J=2.7 Hz,8.7 Hz Ar-H),6.708~6.740(d,1H, J=9.6 Hz, Ar-H), 6.820~6.828(d,1H,2.4 Hz, Ar-H),7.089~7.117(d,1H,J=2.4 Hz,Ar-H),7.503~7.544(dd,1H,2.7 Hz,9.6 Hz, Ar-H),7.595(s, 1H, Ar-H).

C. Preparation of 1-(3-Chloropropyl)-4-Methylpiperazine

The preparation of 1-(3-chloropropyl)-4-methylpiperazine includes steps of: chilling 0.1 mol of piperidine on ice, chilling 100 mL of acetone and 0.125 mol of sodium hydrate (25%) below 5° C.; slowly adding 0.1 mol of 1-chloro-3-bromopropane dropwise; reacting for 48 hours at room temperature 25° C.; vacuum-evaporating solvent to dryness; adding 50 mL of water; extracting by methylene dichloride (3×50 mL); combining organic phases; drying by sodium sulphate overnight; filtering; vacuum-evaporating to get an oily product; adding concentrated hydrochloric acid dropwise to regulate pH value to 1-2; adding methylene dichloride and stirring to remove 1-chloro-3-bromopropane; dissolving the filter residue by adding an amount of water; regulating pH value to 12 by 25% sodium hydroxide; extracting by methylene dichloride (20 ml×3); drying by sodium sulphate; filtering and vacuum-evaporating to obtain a yellow oily product with a yield of 14.2%. $^1$H-NMR(CDCl$_3$,300 MHz) δ: 1.930~1.999 (m,2H,—CH$_2$—),2.301(s,3H,—CH$_3$),2.470~2.517(m, 10H,—CH$_2$—),3.575~3.619(t,2H,—CH$_2$).

D. Preparation of 1-(2-Chloro-4-((3-(4-Methylpiperazin-1-yl)Propyl)Amino)Phenyl)-5-(Trifluoromethyl)Pyridin-2(1H)-One The preparation of 1-(2-chloro-4-((3-(4-methylpiperazin-1-yl)propyl)amino)phenyl)-5-(trifluoromethyl)pyridin-2 (1H)-one includes steps of: adding 15 mL of normal butanol to dissolve 2.59 g (0.003 mol) of 1-(4-amino-2-chlorophenyl)-5-(trifluoromethyl)pyridin-2(1H)-one; adding 0.528 g(0.001 mol) of 1-(3-chloro)propyl-4-methylpiperazine and uniformly mixing; and adding a catalytic amount of potassium iodide; carrying out microwave reaction at 170° C.; filtering; removing solvent from the filtrate through evaporating; and separating residue by column chromatography with eluent of petroleum ether and ethyl acetate with proportion of 1:1 (1% triethylamine) to obtain 0.15 g of yellow solid. m.p.: 129-132° C. ESI-MS(m/z): 429[M+H]$^+$. $^1$H-NMR(CDCl$_3$, 300 MHz) δ ppm: 1.805~1.845(m,2H,—CH$_2$—),2.369(s, 3H,—CH$_3$),2.534~2.575(t,10H,—CH$_2$—),3.201(br,2H,—CH$_2$—), 5.501(br,1H,—NH—),6.516~6.553(dd,1H,J=2.4 Hz,8.7 Hz,Ar-H),6.678~6.734(dd,1H,J=2.4 Hz, 7.2Hz,Ar-H),7.071~7.100(d,1H,J=8.7 Hz,Ar-H),7.491~7.532(dd,1H, J=2.7 Hz,9.6 Hz,Ar-H), 7.604(s,1H,Ar-H).

Example 2

Preparation of 1-(2-Chloro-4-((3-Morpholinylpropyl) Amino)Phenyl)-5-(Trifluoromethyl)Pyridin-2(1H)-One

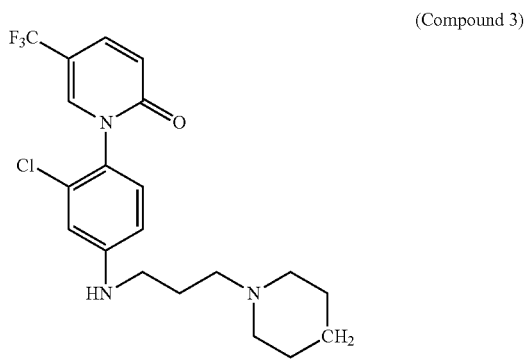

(Compound 2)

The preparation of 1-(2-chloro-4-((3-morpholinylpropyl) amino)phenyl)-5-(trifluoromethyl)pyridin-2(1H)-one includes steps of: adding 5 mL of normal butanol to dissolve 0.54 g (0.003 mol) of 1-(4-amino-2-chlorophenyl)-5-(trifluoromethyl)pyridin-2(1H)-one; adding 0.528 g(0.001 mol) of 1-(3-chloro)propyl-morpholine and a catalytic amount of potassium iodide and uniformly mixing; carrying out microwave reaction at 180° C.; filtering, evaporating filtrate to dryness; and separating residues by chromatography with eluent of petroleum ether and ethyl acetate with proportion of 1:1 (1% triethylamine) to obtain 0.16 g of a yellow solid. m.p.: 95-97° C., ESI-MS(m/z): 416[M+H]$^+$. $^1$H-NMR (CDCl$_3$,300 MHz) δ ppm: 1.836~1.856(m,2H,—CH$_2$—), 2.527(br,6H,—CH$_2$—),3.202~3.258(t,2H,—CH$_2$—),3.777 (br,4H,—CH$_2$—),5.403(br,1H,—NH—),6.523~6.559(dd, 1H,J=2.4 Hz,8.7 Hz,Ar-H),6.689~6.698(d,1H,J=2.7 Hz,Ar-H),6.737(s,1H,Ar-H), 7.078~7.138d,1H,J=8.7 Hz,Ar-H), 7.493~7.534(dd,1H,J=2.7 Hz,9.9 Hz,Ar-H),7.604(s,1H,Ar-H).

Example 3

Preparation of 1-(2-Chloro-4-((3-Piperidin-1-yl)Propylamino)Phenyl)-5-(Trifluoromethyl)Pyridin-2(1H)-One

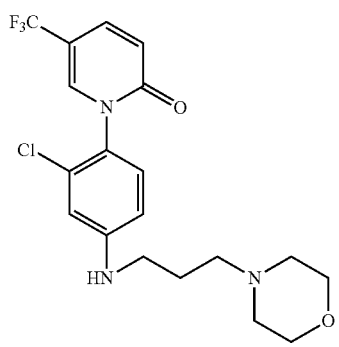

(Compound 3)

The preparation of 1-(2-chloro-4-((3-piperidin-1-yl)propylamino)phenyl)-5-(trifluoromethyl)pyridin-2(1H)-one includes steps of: adding 15 mL of normal butanol to dissolve 3.50 g (0.012 mol) of 1-(4-amino-2-chlorophenyl)-5-(trifluoromethyl)pyridin-2(1H)-one; adding 0.528 g (0.004 mol) of 1-(3-chloro)propylpiperidine and uniformly mixing; and adding a catalytic amount of potassium iodide; carrying out microwave reaction at 180° C.; filtering; evaporating filtrate to dryness; and separating residue by column chromatography with eluent of petroleum ether and ethyl acetate with proportion of 1:1 (1% triethylamine) to obtain 0.21 g of light brown solid. m.p.: 112-115° C., EI-MS(m/z): 413[M]$^+$, $^1$H-NMR(CDCl$_3$,300 MHz) δ ppm: 1.482-1.489 (m,2H), 1.607~1.642 (m,4H), 1.736~1.843 (m,2H), 2.425~2.491 (m,6H), 3.185 (br,2H), 6.011 (br,1H-NH—), 6.499~6.537 (dd,1H,J=2.7 Hz, 8.7 Hz, Ar-H), 6.654~6.662 (d,1H,J=2.4 Hz, Ar-H), 6.698~7.731 (d,1H,J=9.9 Hz, Ar-H), 7.059~7.088 (d,1H,J=8.7 Hz, Ar-H), 7.483~7.524 (dd,1H,J=2.7 Hz, 9.9 Hz, Ar-H), 7.607 (s,1H, Ar-H).

Example 4

Preparation of 1-(4-((3-Butoxypropyl)Amino)-2-Chlorophenyl)-5-(Trifluoromethyl)Pyridin-2(1H)-One (Compound 4)

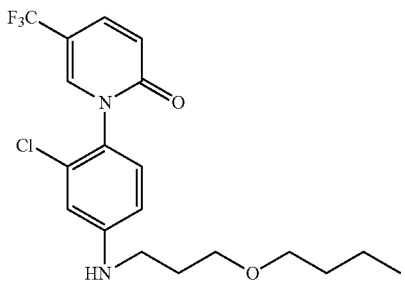

The preparation of 1-(4-((3-butoxypropyl)amino)-2-chlorophenyl)-5-(trifluoromethyl)pyridin-2(1H)-one includes steps of: adding 15 mL of normal butanol to dissolve 2.88 g (0.01 mol) of 1-(4-amino-2-chlorophenyl)-5-(trifluoromethyl)pyridin-2(1H)-one; adding 3.14 g (0.02 mol) of 1-chloro-3-bromopropane for uniformly mixing; and feeding a catalytic amount of potassium iodide; carrying out microwave reaction at 180 DEG C; filtering; evaporating filtrate to dryness; and separating residue by column chromatography with eluent of petroleum ether and ethyl acetate with proportion of 3:1 (1% triethylamine) to obtain 0.20 g of off-white solid. m.p.: 83.0-85.0° C. ESI-MS(m/z): 425[M+N$a$]$^+$, $^1$H-NMR(CDCl$_3$,300 MHz) δ ppm: 0.921~0.970 (t, 3H, —CH$_3$), 1.364~1.439 (m,2H,—CH$_2$—),1.563~1.612 (m,2H,—CH$_2$—), 1.880~1.919 (m,2H,—CH$_2$—), 3.213~3.255 (t,H,—CH$_2$—), 3.415~3.458 (t,2H,—CH$_2$—), 3.542~3.579 (t,2H,—CH$_2$—), 4.696 (br,1H,—NH—), 6.508~6.545 (dd,1H,J=2.4 Hz,2.4 Hz,Ar-H), 6.680~6.689 (d,1H,J=2.7 Hz,Ar-H), 0.704~6.736 (d,1H,J=9.6 Hz,Ar-H), 7.070~7.099 (d,1H,J=8.7 Hz,Ar-H), 7.491~7.532 (dd,1H, J=2.7 Hz,2.4 Hz,Ar-H), 7.606 (s,1H,Ar-H).

Example 5

Preparation of 1-(2-Chloro-4-((2-Hydroxyethyl)Amino) Phenyl)-5-(Trifluoromethyl)Pyridin-2(1H)-One (Compound 5)

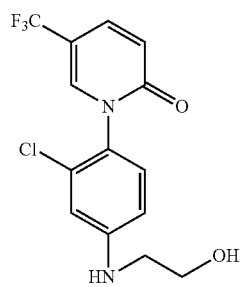

The preparation of 1-(2-chloro-4-((2-hydroxyethyl)amino)phenyl)-5-(trifluoromethyl)pyridin-2(1H)-one includes steps of: adding 12 mL of chloroethanol and 12 mL of DMF to dissolve 0.57 g (0.002 mol) of 1-(4-amino-2-chlorophenyl)-5-(trifluoromethyl)pyridin-2(1H)-one; adding 0.56 g (0.004 mol) of potassium carbonate; mixing for reaction for 12 hours at 130° C.; filtering; evaporating filtrate to dryness; and separating residue by column chromatography with eluent of petroleum ether and ethyl acetate with proportion of 1:1 to obtain 0.080 g of brown solid. m.p.: 161.0-164.0° C., EI-MS(m/z): 332[M]$^+$, $^1$H-NMR(CDCl$_3$,300 MHz) δ ppm: 3.504~3.543 (t,2H,—CH$_2$—), 3.658~3.709 (t,2H—CH$_2$—), 4.412 (br,1H,—NH—), 6.590~6.627 (dd, 1H,J=2.7 Hz,2.4 Hz,Ar-H), 710~6.742 (d,1H,J=9.6 Hz,Ar-H), 6.754~6.762 (d,1H,J=2.4 Hz,Ar-H), 7.128~7.157 (d,1H, J=8.7 Hz,Ar-H), 7.500~7.542 (dd,1H,J=2.7 Hz,9.6 Hz,Ar-H), 7.597 (s,1H,Ar-H).

Example 6

Preparation of 1-(4-(N,N-(2-Hydroxyethyl)Amino)-2-Chlorophenyl)-5-(Trifluoromethyl)Pyridin-2(1H)-One (Compound 6)

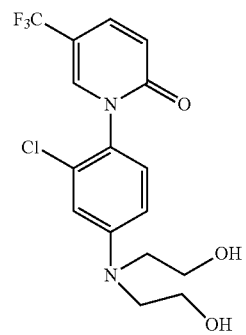

The preparation of 1-(4-(N,N-(2-hydroxyethyl)amino)-2-chlorophenyl)-5-(trifluoromethyl)pyridin-2(1H)-one includes steps of: adding 12 mL of chloroethanol and 12 mL of DMF to dissolve 0.57 g (0.002 mol) of 1-(4-amino-2-chlorophenyl)-5-(trifluoromethyl)pyridin-2(1H)-one; adding 0.56 g (0.004 mol) of potassium carbonate; mixing for reaction for 12 hours at 130 DEG C; filtering; evaporating filtrate to dryness; and separating residue by column chromatography with eluent of petroleum ether and ethyl acetate with proportion of 1:1 to obtain 0.070 g of red brown solid. m.p.: 169.0~172.0° C., EI-MS (m/z): 376[M]$^+$, $^1$H-NMR(CDCl$_3$, 300 MHz) δ ppm: 3.213~3.245 (t,4H,—CH$_2$—), 3.661~3.754 (t,4H—CH$_2$—), 6.714~6.746 (d,1H,J=9.6 Hz,Ar-H), 6.864~6.903 (dd,1H,J=2.7 Hz,9.6 Hz,Ar-H), 7.018~7.027 (d,1H,J=2.7 Hz,Ar-H), 7.214~7.244 (d,1H, J=9.0 Hz,Ar-H), 7.505~7.514 (dd,1H,J=2.7 Hz,Ar-H).

Example 7

Preparation of 1-(2-Chloro-4-(((3-Piperidin-1-yl)Propyl) Amino)Phenyl)-5-(Trifluoromethyl)Pyridin-2(1H)-One Hydrochloride (Compound 7)

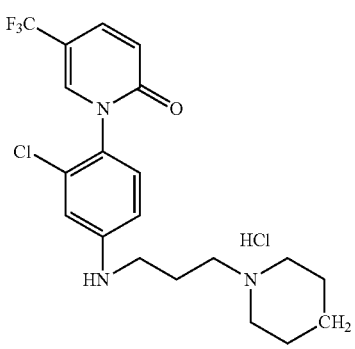

The preparation of 1-(2-chloro-4-(((3-piperidin-1-yl)propyl)amino)phenyl)-5-(trifluoromethyl)pyridin-2(1H)-one hydrochloride includes steps of: dissolving 2.9 mmol of 1-(4-(((3-piperidin-1-yl)propyl)amino)-2-chlorophenyl)-5-(trifluoromethyl)pyridin-2(1H)-one by an amount of ethanol; adding 2 mmol of hydrochloric acid; mixing for reaction for 2 hours; evaporating solvent to dryness to obtain 0.12 g of 1-(2-chloro-4-(((3-piperidin-1-yl)propyl)amino)phenyl)-5-(trifluoromethyl)pyridin-2(1H)-one hydrochloride as an off-white solid. M.P.: 192~195° C., EI-MS(m/z): 414[M+H]$^+$, $^1$H-NMR(D$_2$O) δ ppm: 1.343~1.718 (m,6H,—CH$_2$—), 1.857~1.905 (2H,—H), 1.956~2.055 (m,2H,—CH$_2$—), 2.829~2.905 (t,2H,—CH$_2$—), 3.122~3.116 (t,2H,—CH$_2$—), 3.221~3.284 (2H—CH$_2$—), 3.445~3.487 (2H—CH$_2$—), 6.764~6.812 (2H,Ar-H), 6.965~6.972 (1H,Ar-H), 7.199~7.228 (1H,Ar-H), 7.785~7.907 (1H,Ar-H), 8.075 (1H, Ar-H).

Example 8

Preparation of 1-(2-Chloro-4-((2-(2-Hydroxyethoxy)Ethyl) Amino)-Phenyl)-5-(Trifluoromethyl)Pyridin-2(1H)-One

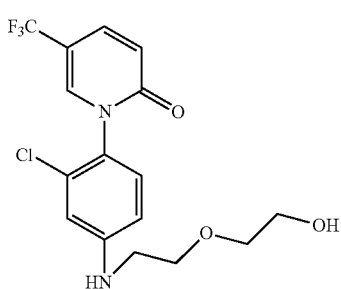

(Compound 8)

The preparation of 1-(2-chloro-4-((2-(2-hydroxyethoxy) ethyl)amino)-phenyl)-5-(trifluoromethyl)pyridin-2(1H)-one includes steps of: dissolving 1-(4-amino-2-chloro)phenyl-5-(trifluoromethyl)pyridin-2(1H)-one and 28 mmol of chloroethoxy ethanol in 50 mL of normal butanol; adding 1.9 mmol of potassium carbonate; carrying out refluxing reaction for 72 hours; filtering; evaporating filtrate to dryness; and separating by column chromatography with eluent of petroleum ether and ethyl acetate with proportion of 1:1 to obtain 0.33 g of a yellow oily product. EI-MS(m/z): 376[M]$^+$, $^1$H-NMR (CDCl$_3$,300 MHz) δ ppm: 3.320~3.355 (t,2H,—CH$_2$—), 3.607~3.637 (t,2H,—CH$_2$—), 3.714~6.748 ((t,2H,—CH$_2$—), 3.768~3.798 ((t,2H,—CH$_2$—), 6.609~6.646 (dd, 1H,J=2.4 Hz, 8.4 Hz,Ar-H), 6.710~6.742 (d,1H,J=9.6 Hz,Ar-H), 6.775~6.783 (d,1H,J=2.4 Hz,Ar-H), 7.107~7.136 (d,1H, J=8.7 Hz,Ar-H), 7.501~7.542 (dd,1H,J=2.7 Hz, 9.6 Hz,Ar-H), 7.603 (s,1H,Ar-H).

Example 9

Preparation of 1-((4-((Piperazin-1-yl)Ethyl)Amino)-2-Chlorophenyl)-5-(Trifluoromethyl)Pyridin-2(1H)-One

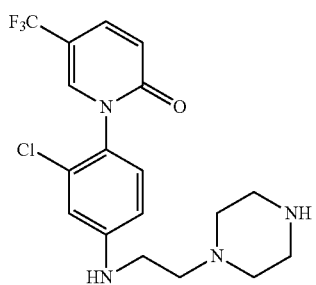

(Compound 9)

A. Preparation of 1-(2-chloro-4-((2-chloroethyl)amino)-phenyl)-5-(trifluoromethyl)pyridin-2(1H)-one The preparation of 1-(2-chloro-4-((2-chloroethyl)amino)-phenyl)-5-(trifluoromethyl)pyridin-2(1H)-one includes steps of: mixing 3 mmol of 1-(2-chloro-4-4-((2-hydroxyethyl) amino)phenyl)-5-(trifluoromethyl)pyridin-2(1H)-one, 120 mL of methylene dichloride, 4.5 mmol of thionyl chloride and 4.5 mmol of triethylamine for reaction for 28 hours at room temperature; and separating by column chromatography with eluent of petroleum ether and ethyl acetate with proportion of 3:1 to obtain 0.5 g of straw yellow solid. M.P.: 160.0~162.0° C., EI-MS(m/z): 350[M]$^+$, $^1$H-NMR(CDCl$_3$,300 MHz) δ ppm: 3.502~3.541 (t,2H,—CH$_2$—), 3.713~3.752 (t,2H,—CH$_2$—), 6.909~6.647 (dd,1H,J=2.7 Hz, 8.7 Hz,Ar-H), 6.716~6.777 (2H,Ar-H), 7.135~7.164 (d,1H,J=8.7 Hz,Ar-H), 7.508~7.550 (dd,1H,J=2.7 Hz, 9.6 Hz,Ar-H), 7.600 (s,1H,Ar-H).

B. Preparation of 1-(2-chloro-4-((2-piperazin-1-yl)ethyl) amino)-phenyl)-5-(trifluoromethyl)pyridin-2(1H)-one dissolving 1.3 mmol of 1-(2-chloro-4-((2-chloroethyl)amino) phenyl)-5-(trifluoromethyl)pyridin-2(1H)-one and 7.8 mmol of anhydrous piperazine in 50 mL of acetonitrile; adding an amount of sodium iodide; carrying out refluxing reaction for 12 hours; filtering; evaporating filtrate to dryness; and separating by column chromatography with eluent of ethyl acetate and methanol with proportion of 5:1 (2% triethylamine) to obtain 0.32 g of yellow colloid substance. EI-MS(m/z): 400 [M]$^+$, $^1$H-NMR(CDCl$_3$,300 MHz) δ ppm: 2.442 (s,4H,—CH$_2$—), 2.628 (s,2H, —CH$_2$—), 2.904 (s,4H,—CH$_2$—), 3.144~3.158 (d,2H,—CH$_2$—), 4.776 (s,1H, —NH—), 6.572~6.60 (d,1H,J=8.4 Hz,Ar-H), 6.707~6.736 (d,1H,J=8.7 Hz,Ar-H), 7.094~7.122 (d,1H,J=8.4 Hz,Ar-H), 7.500~7.530 (d,1H,J=9.0 Hz,Ar-H), 7.609 (s,1H,Ar-H).

Example 10

Preparation of 1-(2-Chloro-4-((2-(Piperidyl-1-yl)Ethyl) Amino)Phenyl)-5-(Trifluoromethyl)Pyridin-2(1H)-One

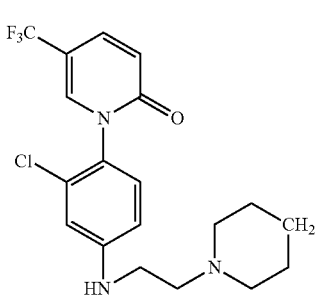

(Compound 10)

The preparation of 1-(2-chloro-4-((2-(piperidyl-1-yl) ethyl)amino)phenyl)-5-(trifluoromethyl)pyridin-2(1H)-one includes steps of: dissolving 1.7 mmol of 1-(2-chloro-4-((2-chloroethyl)amino)phenyl)-5-(trifluoromethyl)pyridin-2 (1H)-one and 10.3 mmol of piperazine in 50 mL of acetonitrile; adding an amount of sodium iodide; carrying out refluxing reaction for 17 hours; filtering; evaporating filtrate to dryness; and separating by column chromatography with eluent of petroleum ether and ethyl acetate with proportion of 1:1 to obtain 0.34 g of yellow colloid substance. EI-MS(m/z): 399[M]$^+$, $^1$H-NMR(CDCl$_3$,300 MHz) δ ppm: 1.470~1.487 (d,2H,J=5.1,—CH$_2$—), 1.576~1.647 (m,4H,—CH$_2$—), 2.436 (s,4H,—CH$_2$—), 2.604~2.644 (t,2H,—CH$_2$—), 3.152~3.165 (d,2H,—CH$_2$—), 4.941 (s,1H,—NH—), 6.568~6.605 (dd,1H,J=2.4 Hz, 8.7 Hz, Ar-H), 6.708~6.734 (t,1H,Ar-H), 7.088~7.117 (d,1H, J=8.7 Hz,Ar-H), 7.493~7.502 (d,1H,J=2.7 Hz,Ar-H), 7.525~7.534 (d,—H, J=2.7 Hz,Ar-H).

Example 11

Preparation of 1-(2-Chloro-4-((2-Morpholinylethyl)Amino)Phenyl)-5-(Trifluoromethyl)Pyridin-2(1H)-One (Compound 11)

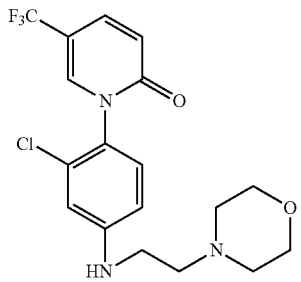

The preparation of 1-(2-chloro-4-((2-morpholinylethyl)amino)phenyl)-5-(trifluoromethyl)pyridin-2(1H)-one includes steps of: dissolving 1.7 mmol of 1-(2-chloro-4-((2-chloroethyl)amino)phenyl)-5-(trifluoromethyl)pyridin-2(1H)-one and 10.9 mmol of morpholine in 50 mL of acetonitrile; adding an amount of sodium iodide; carrying out refluxing reaction for 24 hours; filtering; evaporating filtrate to dryness; and separating by column chromatography with eluent of petroleum ether and ethyl acetate with proportion of 1:1 to obtain 0.67 g of yellow colloid substance. EI-MS(m/z): 401[M]$^+$, $^1$H-NMR(CDCl$_3$,300 MHz) δ ppm: 2.500 (s,4H,—CH$_2$—), 2.650~2.688 (t,2H,—CH$_2$—), 3.150~3.204 (m,2H,—CH$_2$—), 3.728~3.758 (t,4H,—C H$_2$—), 4.781 (s,1H), 6.573~6.610 (dd,1H,J=2.4 Hz,6.0 Hz,Ar-H), 6.703~6.743 (t,2H,Ar-H), 7.098~7.127 (d,1H,J=8.7 Hz,Ar-H), 7.494~7.535 (dd,1H,J=2.7 Hz,9.6 Hz,Ar-H), 7.603 (s,1H, Ar-H).

Example 12

Preparation of 1-(2-Chloro-4-((2-(4-Methylpiperazin-1-yl)Ethyl)Amino)-Phenyl)-5-(Trifluoromethyl)Pyridin-2(1H)-One (Compound 12)

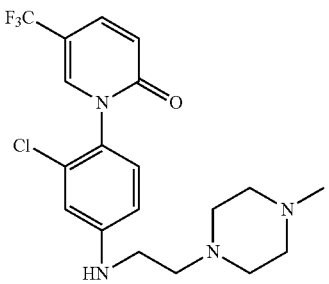

The preparation of 1-(2-chloro-4-((2-(4-methylpiperazin-1-yl)ethyl)amino)-phenyl)-5-(trifluoromethyl)pyridin-2(1H)-one includes steps of: dissolving 1.7 mmol of 1-(2-chloro-4-((2-chloroethyl)amino)phenyl)-5-(trifluoromethyl)pyridin-2(1H)-one and 10.9 mmol of N-methyl piperazine in 50 mL of acetonitrile; adding an amount of sodium iodide; carrying out refluxing reaction for 22 hours; filtering; evaporating filtrate to dryness; and separating by column chromatography with eluent of petroleum ether and ethyl acetate with proportion of 1:1 to obtain 0.70 g of yellow solid. m.p.: 113.1~115.2, EI-MS(m/z): 414[M]$^+$, $^1$H-NMR(CDCl$_3$, 300 MHz) δ ppm: 2.321(s,3H,—CH$_3$), 2.511 (br,8H,—CH$_2$—), 2.639~2.678 (t,2H,—CH$_2$—), 3.126~3.181 (q,2H,—CH$_2$—), 4.736~4.765 (t,1H,—NH—), 6.566~6.603 (dd,1H, J=2.4 Hz, 8.7 Hz,Ar-H), 6.708~6.740 (t,2H,Ar-H), 7.096~7.125 (d,1H, J=9.6 Hz,Ar-H), 7.496~7.537 (dd,1H, J=2.7 Hz, 9.6 Hz,Ar-H), 7.609 (s,1H,Ar-H).

Example 13

Preparation of 1-(2-Chloro-4-((2-(4-(2-Hydroxyethyl)Piperazin-1-yl)Ethyl)Amino)Phenyl)-5-(Trifluoromethyl) Pyridin-2(1H)-One (Compound 13)

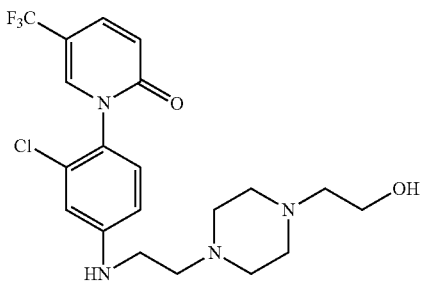

The preparation of 1-(2-chloro-4-((2-(4-(2-hydroxyethyl) piperazin-1-yl)ethyl)amino)phenyl)-5-(trifluoromethyl) pyridin-2(1H)-one includes steps of: dissolving 1.7 mmol of 1-(2-chloro-4-((2-chloroethyl)amino)phenyl)-5-(trifluoromethyl)pyridin-2(1H)-one and 10.9 mmol of hydroxyethyl piperazine in 50 mL of acetonitrile; adding an amount of sodium iodide; carrying out refluxing reaction for 24 hours; filtering; evaporating filtrate to dryness; and separating by column chromatography with eluent of petroleum ether and ethyl acetate with proportion of 1:1 to obtain 0.51 g of yellow colloid substance. EI-MS(m/z): 444[M]$^+$, $^1$H-NMR(CDCl$_3$, 300 MHz) δ ppm: 2.567~2.691 (m,12H, —CH$_2$—), 3.139~3, 1924 (t,2H,—CH$_2$—), 3.632~3.667 (t,2H,—CH$_2$—), 4.737 (br,1H,—NH—), 6.563~6.600 (dd,1H,J=2.4 Hz, 8.7 Hz,Ar-H), 6.702~6.738 (t,2H,Ar-H), 7.094~7.123 (d,1H,J=8.7 Hz,Ar-H), 7.492~7.533 (dd,1H, J=2.7 Hz, 9.0 Hz,Ar-H), 7.603 (s,1H,Ar-H).

Example 14

Inhibition Test of Compounds on NIH3T3 Fibroblasts

An MTT method is used and comprises steps of: culturing cells in DMEM culture medium including 5% calf serum and preparing the cells into cell suspension of 3×10$^4$/ml; inoculating in 96-well plate according to 100 μl/well; transferring new culture medium including compounds with different concentration, fluorofenidone and 1% calf serum after cells are adhered, wherein three repeated wells are provided for each concentration; respectively adding 100 μl of MTT solution in each well after 48 hours and 72 hours of administrating (the culture medium is prepared into 5 mg/ml and kept in dark after filtering), sucking out MTT after 4 hours; adding 150 μl of DMSO which is the dissolving liquid of MTT; after 10 min and MTT is completely dissolved, measuring OD value by ELISA reader; calculating IC50 values of fluorofenidone and measured compounds according to inhibition ratio; calculating multiple of activities of measured compounds and fluorofenidone according to IC50 values of fluorofenidone and measured compounds; and obtaining relative IC50 value of measured compounds according to multiple and IC50 value of fluorofenidone on a certain plate.

Inhibition activity of measured compounds to NIH3T3 fibroblasts

| Measured compounds | 48 hours | | 72 hours | |
|---|---|---|---|---|
| | Relative IC50 (mM) | Multiple | Relative IC50 (mM) | Multiple |
| Fluorofenidone | 4.43 | | 3.52 | |
| Compound 1 | 0.286 | 15.50 | 0.163 | 21.60 |
| Compound 2 | 0.241 | 18.36 | 0.161 | 21.87 |
| Compound 3 | 0.238 | 18.60 | 0.065 | 54.0 |
| Compound 4 | 0.702 | 6.31 | 0.311 | 11.31 |
| Compound 5 | 1.380 | 3.21 | 0.632 | 5.57 |
| Compound 6 | 0.641 | 6.91 | 0.587 | 6.00 |
| Compound 7 | 0.259 | 17.09 | 0.049 | 71.17 |
| Compound 8 | 0.487 | 9.09 | 0.332 | 10.59 |
| Compound 10 | 0.214 | 20.73 | 0.062 | 56.50 |
| Compound 11 | 0.174 | 25.50 | 0.056 | 62.50 |
| Compound 12 | 0.330 | 13.42 | 0.106 | 33.33 |
| Compound 13 | 0.100 | 44.14 | 0.062 | 57.20 |

Notes:
multiple is IC50 value of compounds to IC50 value of fluorofenidone

Example 15

Observation of Treatment Effect of Compound 13 in a Rat Unilateral Ureteral Obstruction Renal Fibrosis Model Materials and Methods 1. Experimental Chemicals The compound 13 is prepared according to the method provided by the invention.

2. Experimental Animals

Nine male SD rats of 188-213 g, coming from Hunan Slac Laboratory Animals Co., Ltd., are illuminated for 12 hours every day; feed is provided by Shanghai Slac Laboratory Animals Co., Ltd.; and drinking water is provided by Department of Laboratory Animal Science of Central South University.

3. Experimental Methods (1) Randomization: nine rats are divided into three groups at random, namely a normal group (n=3); a model group (n=3) and a treatment group (n=3) treated by compound 13 of 15 mg/kg; three rats are in a hutch; and the experimental animals are adaptively fed for two days.

(2) Unilateral ureteral obstruction modeling:

The unilateral ureteral obstruction modeling comprises steps of: lumbar-injecting each rat with 10% chloral hydrate according to 0.35 ml/100 g for anesthesia, fixing on a rat fixing plate; wetting the back skin by water, tightening the skin; unhairing by elbowed surgical scissors in a way closely attaching the skin; sterilizing drape in a conventional way; making an incision of 1.0 cm in longitudinal direction at a junction of a position 1.0 cm below left costal margin and 0.8 cm next to median line of vertebral column; separating successive layers to expose left kidney and left ureter; tying off left ureter against lower pole of left kidney by a thread of 4.0 and another portion 1.0 cm therebelow; isolating ureter between those two points; flushing abdominal cavity by gentamicin physiological saline solution; and stitching successive layers of retroperitoneal space and back skins after no leakage and hemorrhage.

(3) Pharmacological intervention: intragastric administration is carried out the day before modeling operation according to one time per day for 12 days; the method is detailed as follows:

a) preparing 0.5% CMCNa solution by adding an amount of 0.9% physiological saline into CMCNa powder and preparing following samples with 0.5% CMCNa solution as solvent.

b) lavaging the normal group with 6 ml/kg.d 0.5% CMCNa for one time per day.

c) lavaging the model group with 6 ml/kg.d 0.5% CMCNa for one time per day.

d) lavaging the treatment group treated by compound 13 at 15 mg/kg with 6 ml/kg.d 0.5% CMCNa for one time per day.

(4) Animal sacrifice and sample collection

On the $11^{th}$ day after operation, each group of rats is respectively sacrificed by lumbar injection of 10% chloral hydrate (0.7-0.9 ml/100 g) to excessive anesthesia, renal tissues on the obstruction side are fixed by 4% formaldehyde, embedded in paraffin and prepared into 4 μm-thick slices for HE staining and Masson staining.

(5) HE staining evaluation standard:

HE stained slices of renal tissues are successively observed in fives fields of view of renal tubulointerstitium on upper left side, upper right side, lower left side, lower right side and middle portion by a low power lens and are evaluated according to eight indexes of renal interstitium lesion: renal tubular epithelial cell vacuolar degeneration, renal tubular ectasia, renal tubular atrophy, red cell cast, protein cast, interstitial edema, interstitial fibrosis and interstitial inflammatory cell infiltration; an average value is calculated as the index of renal tubulointerstitial lesion of the sample; and the evaluation standard is based on the reference of Radford M G Jr, Donadio J V Jr, Bergstralh E J, et al. Predicting renal outcome in IgA nephropathy. J Am Soc Nephrol, 1997, 8(2):199-207.

(6) Masson Staining Evaluation Standard

Masson staining slices of renal tissues are observed in 20 fields of vision for each sample at random under 400X light microscope; percent of blue-stain collagens in the fields of vision is calculated; an average value is determined after semi-quantitative evaluation: no positive staining, 0; <25%, 1; 25-50%, 2; 50-75%, 3; >75%, 4; and the evaluation standard is based on references. Lin S L, Chen R H, Chen Y M, et al. Pentoxifylline Attenuates Tubulointerstitial Fibrosis by Blocking Smad3/4-Activated Transcription and Profibrogenic Effects of Connective Tissue Growth Factor. J Am Soc Nephrol.2005, 16: 2702-2713.

4. Statistical methods: analytical method of variance of single factor is adopted.

Experimental Results

1. Pathological Evaluation Results of Renal Interstitium Lesions through HE Staining

TABLE 1 comparison of indexes of renal tubulointerstitial lesions of obstruction kidneys of rats in groups

| Group | Number | Score($\overline{X} \pm S$) |
|---|---|---|
| Normal group | 3 | 0.33 ± 0.12 |
| Model group | 3 | 9.00 ± 1.00☆☆☆ |
| Compound 13 group | 3 | 7.00 ± 0.35☆☆** |

Notes:
comparison to normal group, ☆p < 0.05; ☆☆p < 0.01; ☆☆☆p < 0.001;
comparison to model group, *p < 0.05,  p < 0.01, * p < 0.001;

2. Pathological Evaluation Results of Renal Interstitium Lesions through MASSON Staining

TABLE 2 evaluation results of renal interstitium collagens of left kidneys of rats in groups through MASSON staining

| Group | Number | Score($\overline{X} \pm S$) |
|---|---|---|
| Normal group | 3 | $0.25 \pm 0.00$ |
| Model group | 3 | $2.45 \pm 0.38$☆☆☆ |
| Compound 13 group | 3 | $1.52 \pm 0.16$☆☆** |

Notes:
comparison to normal group, ☆$p < 0.05$, ☆☆$p < 0.01$; ☆☆☆$p < 0.001$;
comparison to model group, *$p < 0.05$, $p < 0.01$, * $p < 0.001$;

Conclusion:

The compound 13 of 15 mg/kg can effectively treat renal fibrosis.

The invention claimed is:

1. A 1-(substituted phenyl)-5-trifluoromethyl-2(1H)pyridone compound, having a formula (XIII),

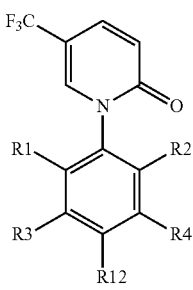

Formula XIII wherein, R1-R4, and R12 are selected from: H, CN, $NO_2$, a hydroxyl group, an amino group, a halogen atom, a $C_1$-$C_6$ alkoxyl group, $NR^{10}R^{11}$, $C(O)R^{14}$, $O-C(O)R^{14}$, a C1-C6 alkyl group, a $C_1$-$C_6$ haloalkyl group, a $C_2$-$C_6$ alkenyl group, a carboxyl group and a carboxylic ether; wherein $R^{14}$ is a $C_1$-$C_6$ alkyl group, $R^{10}$ and $R^{11}$ are selected from H, a $C_1$-$C_6$ alkyl group, a $C_1$-$C_6$ hydroxyalkyl group, an esterified $C_1$-$C_6$ hydroxyalkyl group, a $C_1$-$C_6$ alkoxyalkyl group, or formula XIV;
and at least one of R1-R4, and R12 is $NR^{10}R^{11}$; and at least one of $R^{10}$ and $R^{11}$ is of the formula XIV,

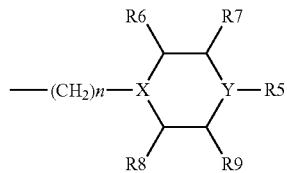

Formula XIV and in formula XIV, R5 is selected from H, a $C_1$-$C_6$ alkyl group, a $C_1$-$C_6$ hydroxyalkyl group, an esterified $C_1$-$C_6$ hydroxyalkyl group and a $C_2$-$C_6$ alkenyl group; R6-R9 are selected from H, a $C_1$-$C_6$ alkoxyl group, =O, a $C_1$-$C_4$ alkyl group, a $C_1$-$C_4$ haloalkyl group, a $C_1$-$C_4$ hydroxyalkyl group, and a $C_2$-$C_4$ alkenyl group; X is selected from N or CH; Y is selected from N, O or C, with the proviso that, when Y is O, $R^5$ is absent; n is 1-6; and pharmaceutically acceptable salts thereof.

2. The 1-(substituted phenyl)-5-trifluoromethyl-2(1H)pyridone compound according to claim 1, wherein R12 is $NR^{10}R^{11}$.

3. The 1-(substituted phenyl)-5-trifluoromethyl-2(1H)pyridone compound according to claim 1, wherein one of R1-R4 is a halogen atom and others are H if R12 is $NR^{10}R^{11}$.

4. The 1-(substituted phenyl)-5-trifluoromethyl-2(1H)pyridone compound according to claim 1, selected from the group consisting of:

1-(2-chloro-4-((3-(4-methylpiperazin-1-yl)propyl)amino)phenyl)-5-(trifluoromethyl)pyridin-2(1H)-one (compound 1);

1-(2-chloro-4-((3-morpholinylpropyl)amino)phenyl)-5-(trifluoromethyl)pyridin-2(1H)-one (compound 2);

1-(2-chloro-4-((3-piperidin-1-yl)propylamino)phenyl)-5-(trifluoromethyl)pyridin-2(1H)-one (compound 3);

1-(4-((3-butoxypropyl)amino)-2-chlorophenyl)-5-(trifluoromethyl)pyridin-2(1H)-one (compound 4);

1-(2-chloro-4-((2-hydroxyethyl)amino)phenyl)-5-(trifluoromethyl)pyridin-2(1H)-one (compound 5);

1-(4-(N,N-(2-hydroxyethyl)amino)-2-chlorophenyl)-5-(trifluoromethyl)pyridin-2(1H)-one (compound 6);

1-(2-chloro-4-(((3-piperidin-1-yl)propyl)amino)phenyl)-5-(trifluoromethyl)pyridin-2(1H)-one hydrochloride (compound 7);

1-(2-chloro-4-((2-(2-hydroxyethoxy)ethyl)amino)phenyl)-5-(trifluoromethyl)pyridin-2(1H)-one (compound 8);

1-((4-((piperazin-1-yl)ethyl)amino)-2-chlorophenyl)-5-(trifluoromethyl)pyridin-2(1H)-one (compound 9);

1-(2-chloro-4-((2-(piperidyl-1-yl)ethyl)amino)phenyl)-5-(trifluoromethyl)pyridin-2(1H)-one (compound 10);

1-(2-chloro-4-((2-morpholinylethyl)amino)phenyl)-5-(trifluoromethyl)pyridin-2(1H)-one (compound 11);

1-(2-chloro-4-((2-(4-methylpiperazin-1-yl)ethyl)amino)phenyl)-5-(trifluoromethyl)pyridin-2(1H)-one (compound 12); and 1-(2-chloro-4-((2-(4-(2-hydroxyethyl)piperazin-1-yl)ethyl)amino)phenyl)-5-(trifluoromethyl)pyridin-2(1H)-one (compound 13).

5. An anti-fibrosis medicament comprising a compound as described in any one of claims 1-4 and a pharmaceutically acceptable excipient.

* * * * *